US011779304B2

(12) United States Patent
Sams et al.

(10) Patent No.: US 11,779,304 B2
(45) Date of Patent: Oct. 10, 2023

(54) ACOUSTIC DAMPING FOR ULTRASOUND IMAGING DEVICES (71) Applicant: BFLY Operations, Inc., Guilford, CT (US)

(72) Inventors: Wayne Sams, Dade City, FL (US); Sarp Satir, San Francisco, CA (US); Jaime Scott Zahorian, Guilford, CT (US); Simon Esteve, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 84 days.

(21) Appl. No.: 16/577,317

(22) Filed: Sep. 20, 2019

(65) Prior Publication Data
US 2020/0093463 A1 Mar. 26, 2020

Related U.S. Application Data (60) Provisional application No. 62/734,497, filed on Sep. 21, 2018.

(51) Int. Cl.
*A61B 8/00* (2006.01)
*G10K 11/00* (2006.01)
*B06B 1/06* (2006.01)

(52) U.S. Cl.
CPC ......... *A61B 8/4444* (2013.01); *A61B 8/4488* (2013.01); *A61B 8/546* (2013.01); *A61B 2562/168* (2013.01); *B06B 1/0681* (2013.01); *G10K 11/002* (2013.01)

(58) Field of Classification Search
CPC ..... A61B 8/4444; A61B 8/546; A61B 8/4488; A61B 8/4411; A61B 8/4483; A61B 2562/168; B06B 1/0681; G10K 11/002
See application file for complete search history.

(56) References Cited

U.S. PATENT DOCUMENTS 4,416,790 A * 11/1983 Schurmann ............. F16F 9/006
                                                    252/62
4,528,652 A    7/1985 Horner et al.
4,787,070 A * 11/1988 Suzuki ................. A61B 8/4281
                                                    181/400

(Continued)

FOREIGN PATENT DOCUMENTS

DE    10142563 A1 *  4/2003  .......... G10K 11/162
EP    0 527 651 A1    2/1993

(Continued)

OTHER PUBLICATIONS

English machine-generated translation of Dos et al. (DE-10142563-A1) (Year: 2021).*

(Continued)

*Primary Examiner* — Christopher Koharski
*Assistant Examiner* — Taylor Deutsch
(74) *Attorney, Agent, or Firm* — Osha Bergman Watanabe & Burton LLP (57) ABSTRACT An ultrasound imaging device includes an ultrasound transducer module disposed within a housing and a flowable acoustic damping material disposed on at least one surface located within an interior of the housing. The flowable acoustic damping material may be a Teflon™-containing gel material, in contact with at least one internal surface of the imaging device to provide acoustic damping.

27 Claims, 7 Drawing Sheets

(56) References Cited

U.S. PATENT DOCUMENTS

| | | | |
|---|---|---|---|
| 9,067,779 | B1 | 6/2015 | Rothberg et al. |
| 9,499,392 | B2 | 11/2016 | Rothberg et al. |
| 9,521,991 | B2 | 12/2016 | Rothberg et al. |
| 9,592,030 | B2 | 3/2017 | Rothberg et al. |
| 10,446,132 | B2 | 10/2019 | Alie et al. |
| 2008/0194963 | A1 | 8/2008 | Randall |
| 2008/0228082 | A1 | 9/2008 | Scheirer et al. |
| 2009/0076393 | A1 | 3/2009 | Adachi et al. |
| 2010/0076315 | A1 | 3/2010 | Erkamp et al. |
| 2010/0228130 | A1 | 9/2010 | Chiang et al. |
| 2010/0249670 | A1 | 9/2010 | Smith et al. |
| 2011/0055447 | A1 | 3/2011 | Costa |
| 2013/0133408 | A1 | 5/2013 | Lang |
| 2013/0345567 | A1 | 12/2013 | Sudol et al. |
| 2014/0128740 | A1 | 5/2014 | Chiang et al. |
| 2014/0165740 | A1 | 6/2014 | Speidel |
| 2014/0269209 | A1 | 9/2014 | Smith et al. |
| 2016/0288169 | A1* | 10/2016 | Bae .............. H01L 41/253 |
| 2017/0135673 | A1 | 5/2017 | Bruestle et al. |
| 2017/0209120 | A1 | 7/2017 | Fujimura |
| 2018/0021014 | A1* | 1/2018 | Chen .............. A61B 8/4444 600/459 |
| 2018/0028159 | A1 | 2/2018 | Hagemen et al. |
| 2018/0078240 | A1 | 3/2018 | Pelissier et al. |
| 2018/0263604 | A1 | 9/2018 | Manning et al. |
| 2019/0180728 | A1 | 6/2019 | Alie et al. |
| 2019/0339387 | A1* | 11/2019 | Pang .............. B06B 1/0622 |
| 2021/0251613 | A1* | 8/2021 | Tavoletti .............. A61B 8/546 |

FOREIGN PATENT DOCUMENTS

| | | | | |
|---|---|---|---|---|
| EP | 0527651 A1 * | 2/1993 | ......... | A61B 8/4209 |
| JP | 2007528153 A | 10/2007 | | |
| JP | 2012100123 A | 5/2012 | | |
| WO | WO 2019/099638 A1 | 5/2019 | | |

OTHER PUBLICATIONS

Schiavone et al., "A highly compact packaging concept for ultrasound transducer arrays embedded in neurosurgical needles", springerlink.com, Jan. 18, 2016, Microsyst Technol (2017) 23:3881-3891. (Year: 2017).*

International Search Report and Written Opinion dated Dec. 6, 2019 in connection with International Application No. PCT/US2019/052051.

[No Author Listed], Innovative Thermally Conductive Silicone Solutions. Enhancing the Performance and Reliability of Your PCB System Assemblies. The Dow Chemical Company. 2018; 8 pages. Retrieved from the Internet: https://www.ellsworth.com/globalassets/literature-library/manufacturer/dow-corning/dow-corning-brochure-enhancing-the-reliability-of-your-electronics-designs.pdf Last accessed Dec. 11, 2019.

[No Author Listed], TEF-GEL Home Page. Ultra Safety Systems. 2008; 1 page. Retrieved from the Internet: http://ultrasafetysystems.com/contain.php?param=tefgel_infor. Last accessed Dec. 11, 2019.

[No Author Listed], TEF-GEL Safety Data Sheet. Ultra Safety Systems. Nov. 7, 2018; 7 pages. Retrieved from the Internet: http://ultrasafetysystems.com/SDS_US_English_Tef-Gel.pdf Last accessed Dec. 11, 2019.

International Preliminary Report on Patentability dated Apr. 1, 2021 in connection with International Application No. PCT/US2019/052051.

Extended European Search Report dated May 4, 2022 in connection with European Application No. EP 19861994.2.

Argoudelis, Comparison of vibration isolators with silicone to anti-vibration products made of natural rubber compounds. Vibro Control Product; XP055481616, Aug. 1, 2014. Retrieved from the Internet: http://antivibration-systems.com/vibration-isolators-silicon-vibration-control-rubber/ [last retrieved on Jun. 6, 2018], 5 pages.

Office Action issued in counterpart Japanese Application No. 2021-511548, dated May 16, 2023 (6 pages).

* cited by examiner

ACOUSTIC DAMPING FOR ULTRASOUND IMAGING DEVICES

CROSS-REFERENCE TO RELATED APPLICATIONS

The present application claims the benefit under 35 U.S.C. § 119(e) of U.S. Provisional Patent Application Ser. No. 62/734,497, filed Sep. 21, 2018 and entitled "ACOUSTIC DAMPING FOR ULTRASOUND IMAGING DEVICES," which is hereby incorporated herein by reference in its entirety.

FIELD

The present disclosure relates generally to ultrasound imaging devices and, more specifically, to structures and techniques for acoustic damping of ultrasound imaging devices.

BACKGROUND

Ultrasound devices may be used to perform diagnostic imaging and/or treatment, using sound waves with frequencies that are higher than those audible to humans. Ultrasound imaging may be used to see internal soft tissue body structures, for example to find a source of disease or to exclude any pathology. When ultrasound pulses are transmitted into tissue (e.g., by using a probe), sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound images.

Some ultrasound imaging devices may be fabricated using micromachined ultrasound transducers, including a flexible membrane suspended above a substrate. A cavity is located between part of the substrate and the membrane, such that the combination of the substrate, cavity and membrane form a variable capacitor. When actuated by an appropriate electrical signal, the membrane generates an ultrasound signal by vibration. In response to receiving an ultrasound signal, the membrane is caused to vibrate and, as a result, an output electrical signal can be generated.

SUMMARY

Some aspects of the present application provide packing of an ultrasound device which includes acoustic damping material. The acoustic damping material may be a gel in some embodiments.

In one aspect, an ultrasound imaging device includes an ultrasound transducer module disposed within a housing and a flowable acoustic damping material disposed on at least one surface located within an interior of the housing.

In another aspect, a method of fabricating an ultrasound imaging device includes applying a flowable acoustic damping material to at least one surface located within an interior of a housing, the housing having an ultrasound transducer module disposed therein.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Medical ultrasound imaging transducers are used to transmit acoustic pulses that are coupled into a patient through one or more acoustic matching layers. After sending each pulse, the transducers then detect incoming body echoes. The echoes are produced by acoustic impedance mismatches of different tissues (or tissue types) within the patient which enable both partial transmission and partial reflection of the acoustic energy. Exemplary types of ultrasonic transducers include those formed from piezoelectric materials or, more recently, micromachined ultrasonic transducers (MUTs) that may be formed using a semiconductor substrate. A capacitive micromachined ultrasonic transducer (CMUT) is one specific example of a MUT device in which a flexible membrane is suspended above a conductive electrode by a small gap. When a voltage is applied between the membrane and the electrode, Coulombic forces attract the flexible membrane to the electrode. As the applied voltage varies over time, so does the membrane position, thereby generating acoustic energy that radiates from the face of the transducer as the membrane moves. However, in addition to transmitting acoustic energy in a forward direction toward the body being imaged, the transducers may simultaneously transmit acoustic energy in a backward direction away from the patient being imaged. That is, some portion of the acoustic energy is also propagated back through the CMUT support structure(s), such as a silicon wafer for example.

When an incident ultrasound pulse encounters a large, smooth interface of two body tissues with different acoustic impedances, the sound energy is reflected back to the transducer. This type of reflection is called specular reflection, and the echo intensity generated is proportional to the acoustic impedance gradient between the two mediums. The same holds true for structures located in a direction away from the patient being imaged, such as a semiconductor chip/metal heat sink interface.

Typically, for both piezoelectric and capacitive transducer devices, an acoustic backing material is positioned on a back side of an ultrasonic transducer array in order to absorb and/or scatter as much of the backward transmitted acoustic energy as possible and prevent such energy from being reflected by any support structure(s) back toward the transducers and reducing the quality of the acoustic image signals obtained from the patient by creating interference. In general, however, materials that have good acoustic attenuating and scattering properties may also have poor thermal conductivity and/or coefficient of thermal expansion (CTE) mismatches with respect to the transducer substrate material. Conversely, materials that have good thermal conductivity may have poor acoustic attenuation capabilities.

In the case of a transducer-on-integrated circuit ultrasound device (such as those produced by the Assignee of the present application, for example), where computing resources are located within the body of an ultrasound probe, and perhaps located proximate a transducing end of the probe body, heat conducting materials (e.g., aluminum or other metals) may be used in the fabrication of the probe body itself to assist in device heat dissipation. In this case, such a heat dissipating probe body may be structurally more rigid than more conventional probe bodies (e.g., plastic). As such, it may be desirable to be able to provide acoustic damping capabilities for ultrasound imaging devices that utilize one or more thermally conductive, rigid housing materials.

Accordingly, exemplary embodiments disclosed herein introduce an ultrasound imaging device that incorporates a flowable acoustic damping material, such as a Teflon™-containing (polytetrafluoroethylene-containing) gel material, in contact with at least one internal surface of the imaging device to provide acoustic damping. One such suitable substance that may be used as the Teflon™-containing gel material for acoustic damping is sold under the trademark Tef-Gel™ by Ultra Safety Systems, Inc. As described by the manufacturer, the Teflon™-containing gel comprises a paste containing 40% PTFE (polytetrafluoroethylene) powder and 0% volatile solvents, with no silicones or petroleum solvents. The gel is marketed and developed as an anti-seize, anti-corrosion lubricant used in corrosive marine environments to prevent galling, seizing and blistering of metals, as well as preventing corrosion between dissimilar metals. Notwithstanding the marketed use for this material, Applicants have advantageously discovered that such a Teflon™-containing gel material also provides acoustic damping properties, in addition to the anticorrosive and lubricating properties the material is conventionally used for.

Figure 1:
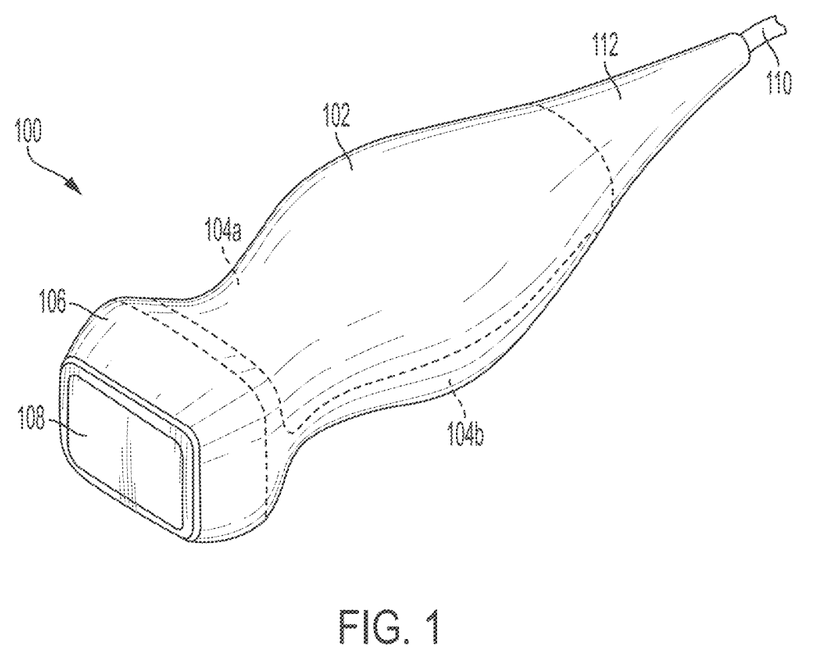
FIG. 1 is a perspective view of an exemplary ultrasound imaging device that may be used in accordance with embodiments of the disclosure.

Referring now to FIG. 1, there is shown a perspective view of an exemplary ultrasound imaging device 100 that may be used in accordance with embodiments of the disclosure. At the outset, it should be appreciated that the device 100 is only example of an ultrasound imaging device with which embodiments of the disclosure may be utilized with, and that other such devices are also contemplated. As illustrated, the ultrasound imaging device 100 includes a probe body 102 that may be a unitary component or, alternatively, may comprise multiple housing components 104a, 104b as indicated by the dashed lines. For example, providing a probe body with multiple components 104a, 104b, may allow for easier assembly of various internal components of the imaging device including, for example, circuit boards, batteries, cable connectors, etc. Disposed at a first (transducing) end of the probe body 102 is a shroud 106 that houses an ultrasound transducer module assembly (described in further detail below). In one embodiment, both the probe body 102 and the shroud 106 are formed from a same material, such as anodized aluminum or anodized aluminum alloys, for example. As indicated above, the probe body 102 and shroud 106 may provide heat dissipating capability and, consequently, may be structurally more rigid than more conventional probe bodies (e.g., plastic).

FIG. 1 further illustrates an acoustic lens 108 disposed at a transducing end of the shroud 106, with the acoustic lens 108 configured to be brought into physical contact with a subject to be imaged. The acoustic lens 108 may be formed, for example, from a room-temperature-vulcanizing (RTV) silicone rubber by mixing a silicone rubber material with a curing agent or vulcanizing agent, followed by degassing to remove any entrained air bubbles from the mixed silicone and catalyst to provide a desired tensile strength.

Disposed at a second end of the probe body 102 is a cable 110 that may be configured to provide a communication path between the ultrasound imaging device 100 and a host device (not shown) such as a smartphone, tablet, computer terminal, display screen and the like. In embodiments where the probe body 102 does not contain an internal power supply, it is contemplated that the cable 110 may also provide power to the ultrasound imaging device from an external power source (not shown). Optionally, a strain relief sleeve 112 may be provided at the second end of the probe body 102 corresponding to a location where the cable 110 mechanically and electrically connects with internal components of the ultrasound imaging device 100. The strain relief sleeve 112 may be a flexible material, such as rubber for example.

Figure 2A:
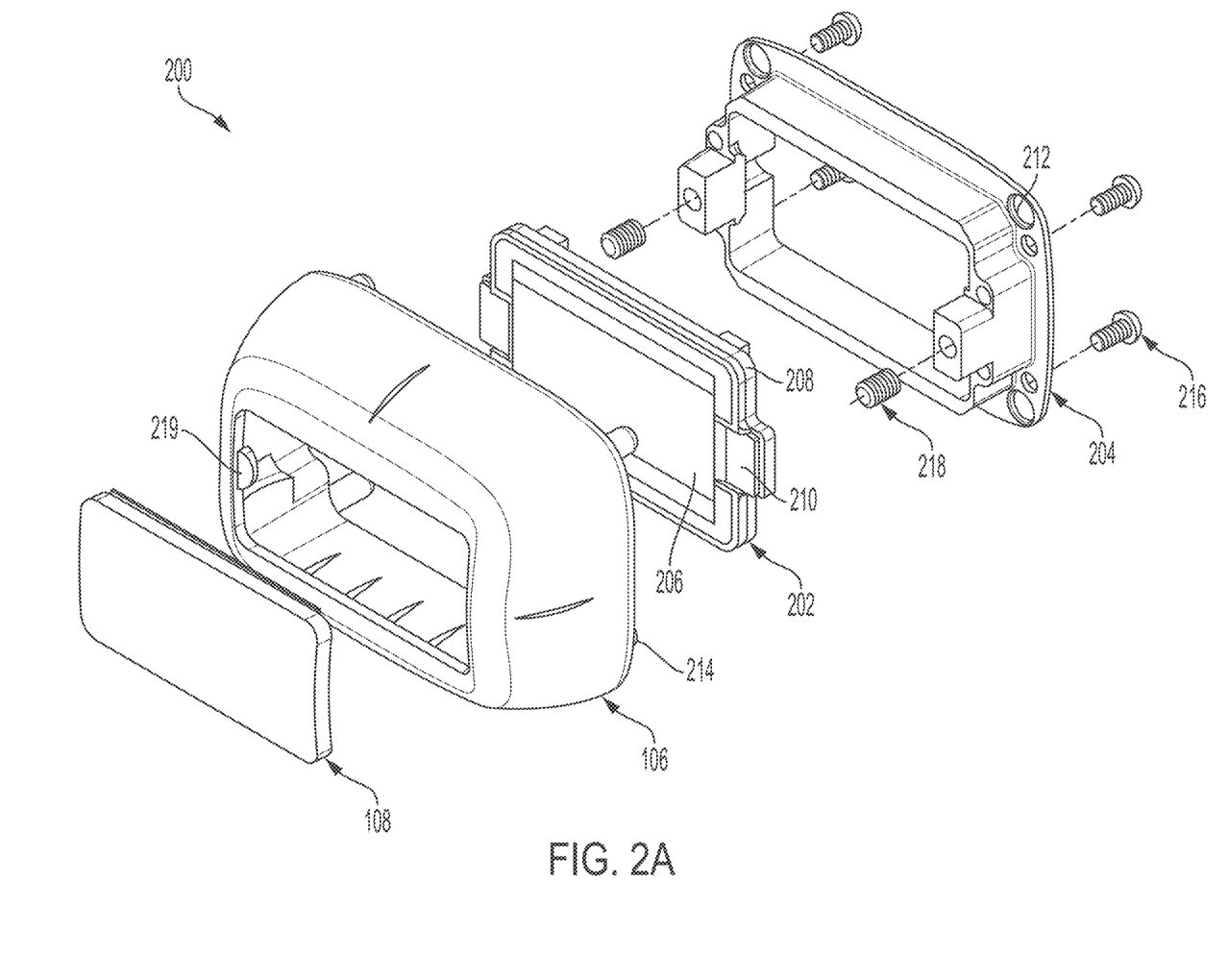
FIG. 2A is an exploded perspective view of an ultrasound transducer module assembly that may comprise a portion of the ultrasound imaging device of FIG. 1.

Referring now to FIG. 2A, there is shown an exploded perspective view of an ultrasound transducer module assembly 200 that may comprise a portion of the ultrasound imaging device 100 of FIG. 1. In addition to the externally disposed shroud 106 and acoustic lens 108, FIG. 2A further illustrates a packaged ultrasound transducer assembly 202 and a heat spreader element 204 that are configured to reside within an interior region of the shroud 106. In the embodiment illustrated, the packaged ultrasound transducer assembly 202 includes a transducer-on-integrated circuit chip stack 206 (hereinafter referred to as an "ultrasound chip" for convenience), a circuit board/interposer 208, and thermal conductive region 210. The heat spreader element 204 is formed from a thermally conductive material, such as aluminum for example, and is provided with openings 212 at an outer perimeter thereof that align and mate with corresponding posts 214 on the shroud 106. Additional hardware, such as for example screws 216 and set screws 218, may be used to help secure the heat spreader element 204 within the inner confines of the shroud 106.

In a fully assembled and operational state of the ultrasound imaging device 100, heat generated by the processing power of the ultrasound chip 206 may be transferred, via the thermal conductive region 210 of the packaged ultrasound transducer assembly 202, to the shroud 106. For example, the thermal conductive region 210 may be placed in thermal contact with tabs 219 of the shroud 106, optionally with an amount of thermal adhesive, grease or paste (not shown) therebetween. The shroud 106 may then direct heat away from the transducing end of ultrasound imaging device 100, to the probe body 102 (FIG. 1), via the heat spreader element 204.

Figure 2B:
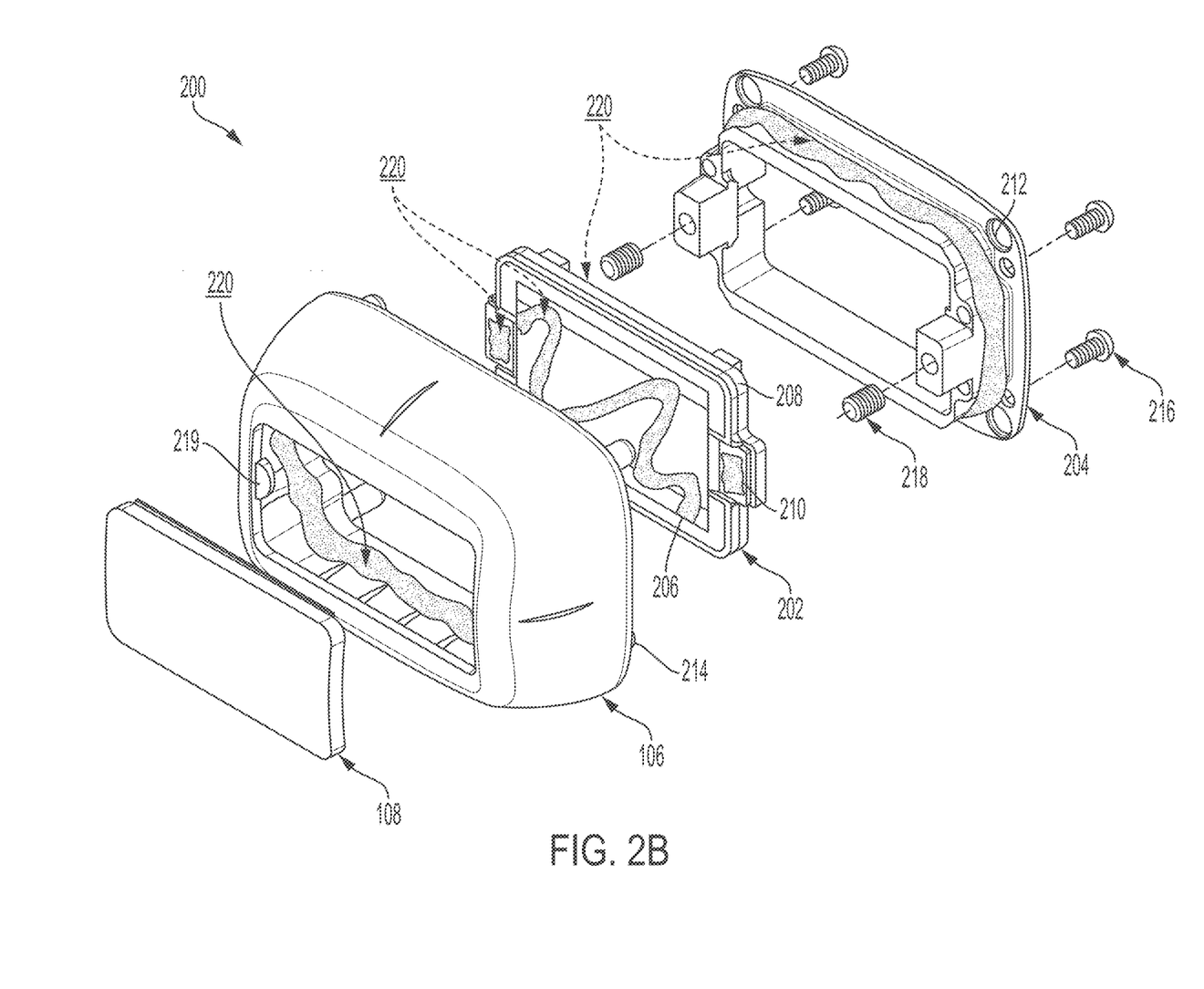
FIG. 2B illustrates exemplary locations on the ultrasound transducer module assembly of FIG. 2A for a flowable acoustic damping material, according to an embodiment.

As indicated above, structures that are relatively good thermal conductors may have less desirable acoustic damping capabilities, and as such Applicants have determined that the placement of a flowable acoustic damping material 220 at one or more locations within the ultrasound transducer module assembly 200 is effective in providing acoustic damping resulting from the operation of the ultrasound transducers of the ultrasound chip 206. In FIG. 2B, the solid arrow illustrates one suitable location for placement of the flowable acoustic damping material 220, which is in contact with an inner perimeter of the shroud 106. However, alternate and/or additional locations for the flowable acoustic damping material 220 are also contemplated as indicated by the dashed arrows in FIG. 2B. Such other locations for the flowable acoustic damping material 220 may include, but are not limited to, the packaged ultrasound transducer assembly 202 (including the chip 206, circuit board 208, thermal conductive region 210) and heat spreader element 204. Moreover, the flowable acoustic damping material 220 could also be provided on interior surfaces of the probe body 102 if desired. In addition to Teflon™-containing gel, it is also contemplated that other flowable acoustic damping materials may also be utilized including, for example, Dow Corning™ 1-4173 thermally conductive adhesive, and butyl rubber. With such alternative flowable acoustic damping materials, curing of such materials may also be utilized.

Figure 3:
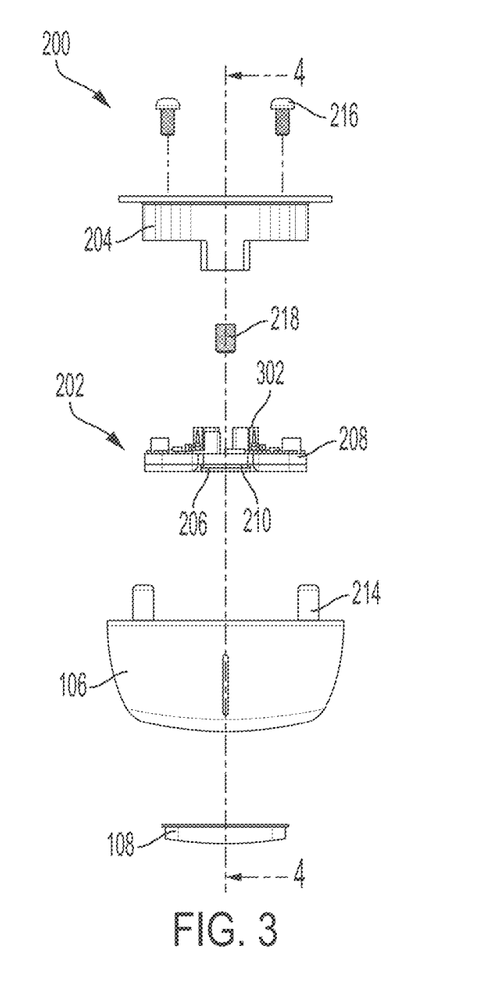
FIG. 3 is an exploded end view of the ultrasound transducer module assembly of FIGS. 2A-2B.
Figure 4:
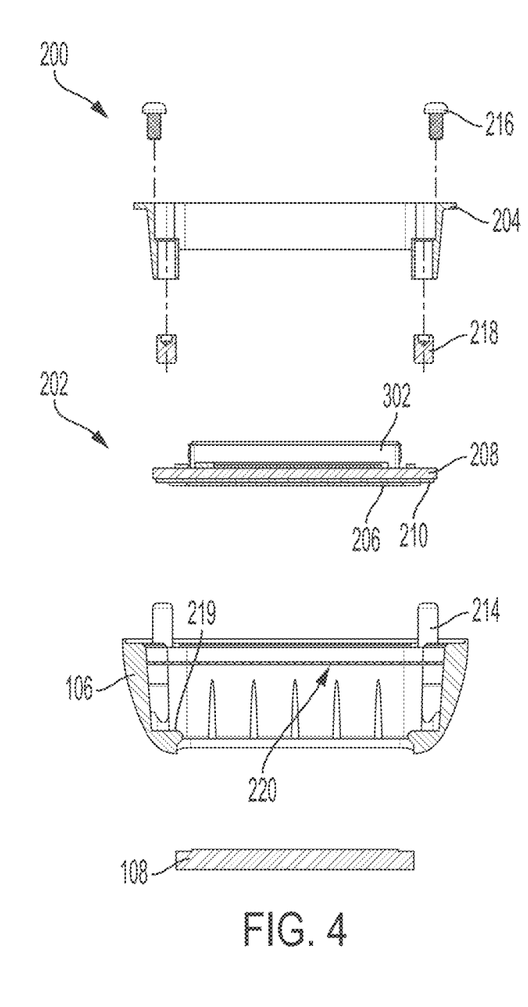
FIG. 4 is an exploded cross-sectional view of the ultrasound transducer module assembly of FIG. 3, viewed along the arrows 4-4.

FIG. 3 and FIG. 4 provide additional views of the ultrasound transducer module assembly 200. More specifically, FIG. 3 is an exploded end view of the ultrasound transducer module assembly of FIGS. 2A-2B, and FIG. 4 is an exploded cross-sectional view of the ultrasound transducer module assembly of FIG. 3, viewed along the arrows 4-4. In addition to the various features illustrated and described in FIGS. 2A-2B, both FIG. 3 and FIG. 4 illustrate a back side of the packaged ultrasound transducer assembly 202, where one or more backplane connectors 302 may be incorporated. The connectors 302 may be mated to corresponding circuit boards (e.g., power boards, field programmable gate array (FPGA) boards, not shown) also included within the housing 102 as part of the ultrasound imaging device 100. As shown in FIG. 4, the horizontal line indicated on the interior surface of the shroud 106 corresponds to a desirable location for application of the flowable acoustic damping material 220.

Figure 5:
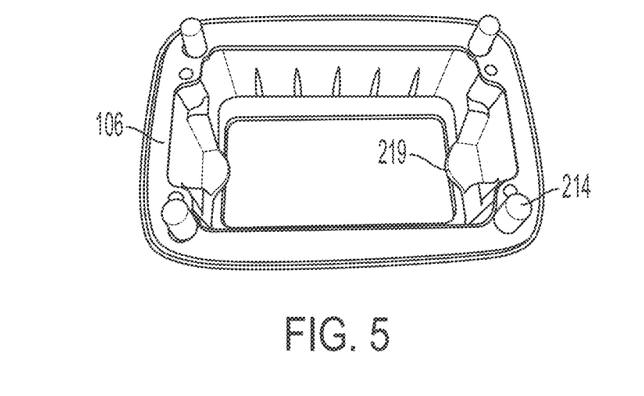
FIG. 5 illustrate an exemplary shroud of the ultrasound transducer module assembly of FIGS. 2-4.
Figure 6:
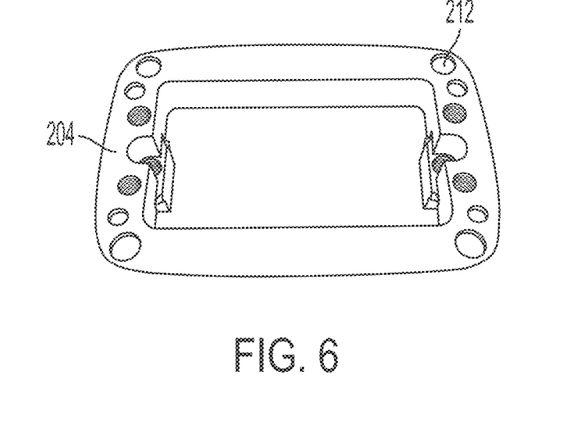
FIGS. 6 and 7 illustrate an exemplary heat spreader element of the ultrasound transducer module assembly of FIGS. 2-4.
Figure 7:
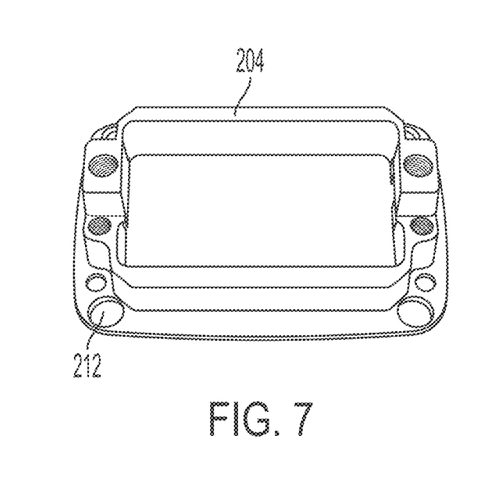

Referring generally to FIGS. 5-8, there are shown various views illustrating some of the assembly steps of the above described ultrasound transducer module assembly 200. FIG. 5 illustrates the shroud 106 and its interior surfaces, including tabs 219, whereas FIGS. 6 and 7 illustrate the heat spreader element 204 that mates with the shroud 106. FIG. 6 shows a top view of the heat spreader element 204, which is the orientation for insertion into the shroud shown in FIG. 5, while FIG. 7 shows a bottom view of the heat spreader element 204. Again, the posts 214 of the shroud 106 are configured to receive the openings 212 of the heat spreader element 204.

Figure 8:
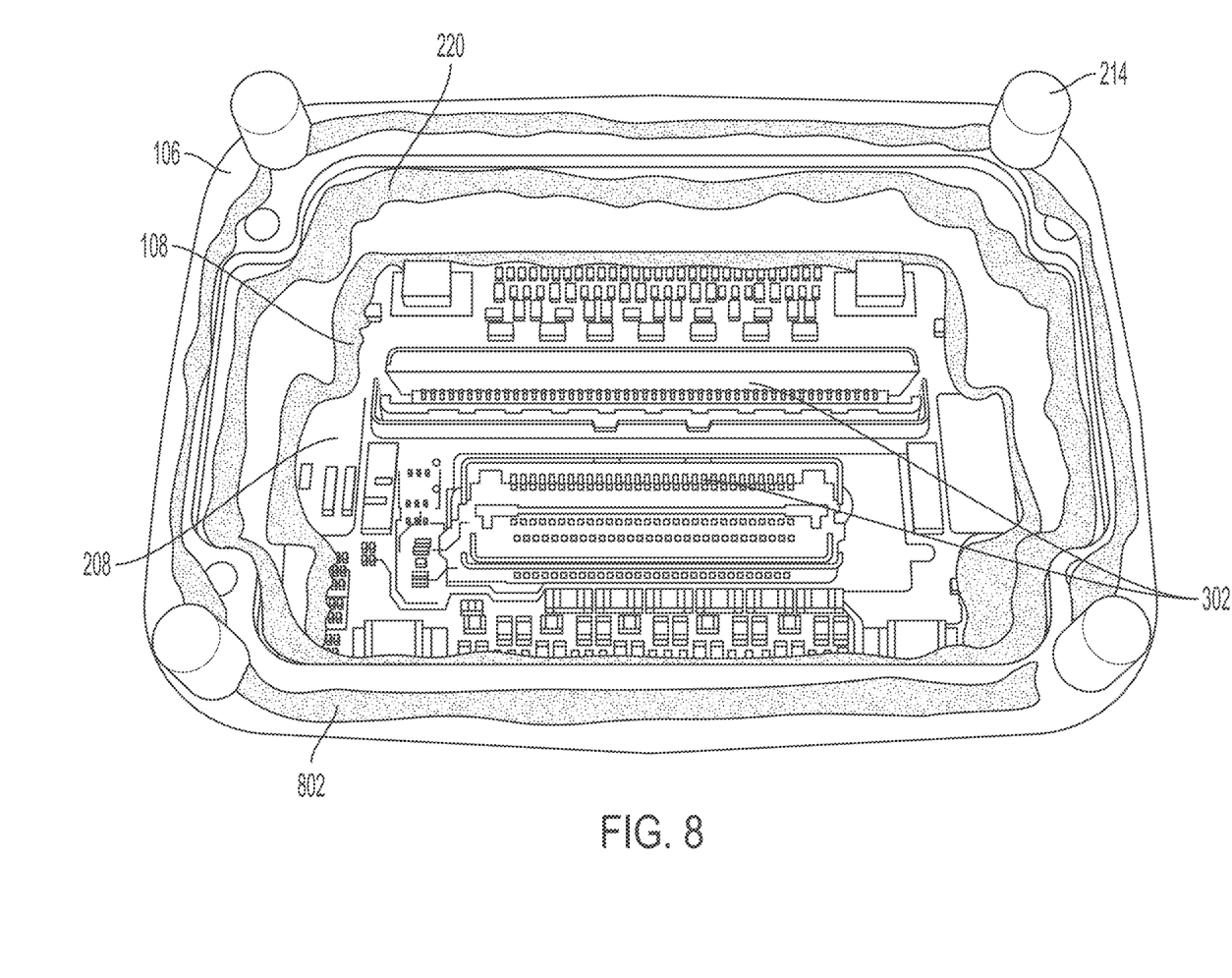
FIG. 8 is illustrates a partially completed ultrasound transducer module assembly, illustrating an exemplary placement location of a flowable acoustic damping material, according to an embodiment.

Referring now to FIG. 8, the packaged ultrasound transducer assembly 202 is shown inserted into the shroud 106. At the point of assembly depicted in FIG. 8, various steps may already be completed including, by way of example only, cleaning of the shroud 106, (e.g., by a plasma clean to active the surface), priming of the interior surface of the shroud 106, application of a thermal paste to the tabs 219 of the shroud 106, and formation of the acoustic lens 108.

Specifically visible in the image of FIG. 8 is the circuit board/interposer 208 and backplane connectors 302 of the packaged ultrasound transducer assembly 202. Portions of the RTV material for the acoustic lens 108 are also visible around the perimeter of the circuit board/interposer 208. As further illustrated in FIG. 8, the flowable acoustic damping material 220 is applied around an interior perimeter of the shroud 106. A layer of thermal paste 802 (e.g., such as a thermal paste manufactured by Arctic Silver company) may optionally be applied around a top edge of the shroud, in preparation for contact with the heat spreader element 204 (not shown in FIG. 8) once inserted.

Figure 9:
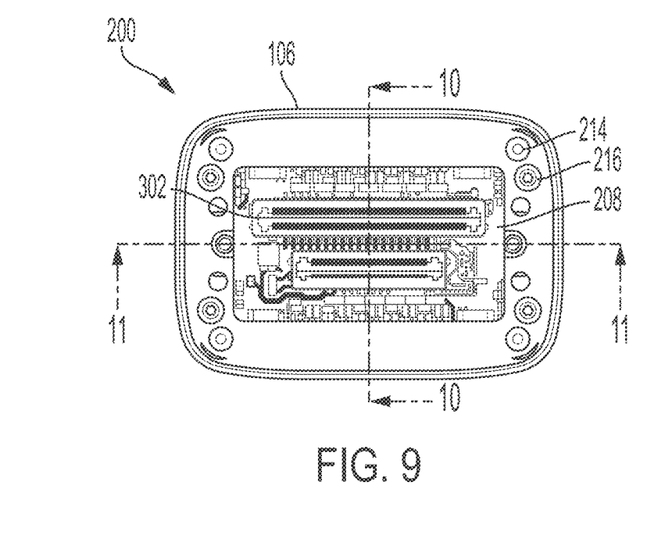
FIG. 9 is a top view of a completed ultrasound transducer module assembly.
Figure 10:
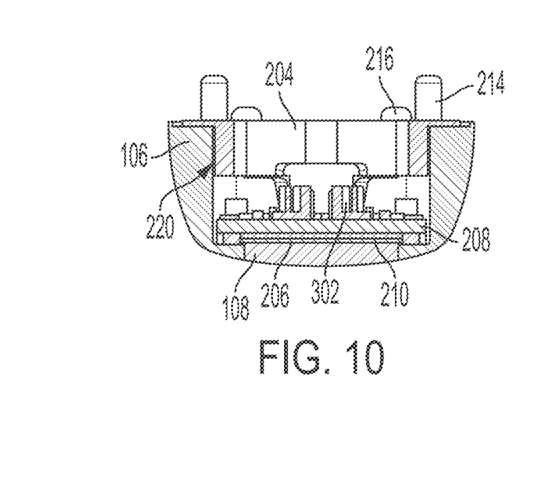
FIG. 10 is a cross-sectional view of the completed ultrasound transducer module assembly of FIG. 9, viewed along the arrows 10-10.
Figure 11:
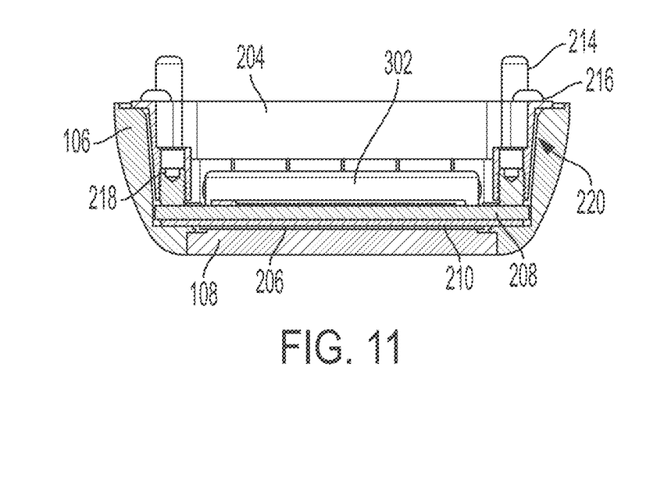
FIG. 11 is a cross-sectional view of the completed ultrasound transducer module assembly of FIG. 9, viewed along the arrows 11-11.

FIGS. 9-11 illustrate the ultrasound transducer module assembly 200 in substantially a fully assembled configuration. Following the application of the flowable acoustic damping material 220 and optionally the thermal paste 802, the heat spreader element 204 is inserted into the shroud 106. The screws 216 and set screws 218 may be torqued to a desired set point, and thereafter tightened. Although not specifically illustrated in FIGS. 9-11, a shroud gasket may also be provided at the outer perimeter of the shroud, outward of the posts 214 before the ultrasound transducer module assembly 200 is fully integrated with the housing 102 of the ultrasound imaging device 100. Arrows in FIG. 10 and FIG. 11 indicate examples of a general location of the applied flowable acoustic damping material 220 following insertion of the heat spreader element 204 into the shroud 106. It is contemplated that some of the acoustic damping material may be pushed further down the interior walls of the shroud 106 as the heat spreader element 204 is inserted therein.

Various aspects of the present application may be used alone, in combination, or in a variety of arrangements not specifically discussed in the embodiments described in the foregoing and is therefore not limited in its application to the details and arrangement of components set forth in the foregoing description or illustrated in the drawings. For example, features described in one embodiment may be combined in any manner with features described in other embodiments.

Also, certain aspects may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound imaging device, comprising:
   a metallic housing;
   a shroud coupled to the metallic housing and disposed at an end of the metallic housing, the shroud and the metallic housing being coupled together to define an interior region;
   a heat spreading structure disposed within the interior region and fastened to the shroud;
   an ultrasound transducer module disposed within the shroud; and
   a bead line of flowable acoustic damping gel or paste disposed at least partially around an inner perimeter of the shroud.

2. The ultrasound imaging device of claim 1, wherein at least one internal surface of the shroud faces at least one surface of the heat spreading structure.

3. The ultrasound imaging device of claim 1, wherein the flowable acoustic damping gel or paste comprises a polytetrafluoroethylene-containing gel.

4. The ultrasound imaging device of claim 1, wherein at least one internal surface of the shroud contacts at least one surface of the heat spreading structure.

5. The ultrasound imaging device of claim 1, wherein the heat spreading structure comprises aluminum.

6. The ultrasound imaging device of claim 1, wherein the shroud comprises a metal material.

7. The ultrasound imaging device of claim 1, wherein the metallic housing comprises aluminum.

8. The ultrasound imaging device of claim 1, wherein the flowable acoustic damping gel or paste is further disposed on the ultrasound transducer module.

9. The ultrasound imaging device of claim 8, wherein the ultrasound transducer module comprises an ultrasound transducer array bonded to an integrated circuit.

10. The ultrasound imaging device of claim 1, wherein the heat spreading structure forms a closed contour that fits at least partially within the shroud, and wherein at least one internal surface of the shroud is adjacent at least one surface of the heat spreading structure.

11. The ultrasound imaging device of claim 10, wherein the flowable acoustic damping gel or paste is further disposed on a rear surface of the heat spreading structure.

12. The ultrasound imaging device of claim 10, wherein the flowable acoustic damping gel or paste is further disposed on a rear surface of the ultrasound transducer module.

13. The ultrasound imaging device of claim 1, wherein the flowable acoustic damping gel or paste comprises polytetrafluoroethylene powder.

14. A method of fabricating an ultrasound imaging device having a shroud disposed at an end of a housing, a heat spreading structure disposed within a region defined by the shroud and the housing, and an ultrasound transducer module disposed within the shroud, the method comprising:
   applying a bead line of flowable acoustic damping gel or paste at least partially around an inner perimeter of the shroud.

15. The method of claim 14, further comprising nesting the heat spreading structure at least partially in the shroud such that the bead line of flowable acoustic damping gel or paste is between at least one inner surface of the shroud and at least one surface of the heat spreading structure.

16. The method of claim 14, wherein the flowable acoustic damping gel or paste comprises a polytetrafluoroethylene-containing gel.

17. The method of claim 14, wherein the applying of the bead line of flowable acoustic damping gel or paste comprises applying the flowable acoustic damping gel or paste in a line.

18. The method of claim 14, further comprising fastening the heat spreading structure within the shroud such that at least one inner surface of the shroud faces at least one surface of the heat spreading structure.

19. The method of claim 18, further comprising applying the flowable acoustic damping gel or paste to a rear surface of the ultrasound transducer module.

20. The method of claim 14, wherein the housing comprises a heat sinking material.

21. The method of claim 20, wherein the housing comprises a metal material.

22. The method of claim 21, wherein the housing comprises aluminum.

23. The method of claim 14, wherein at least one surface of the heat spreading structure is outwardly facing.

24. The method of claim 14, further comprising fastening the heat spreading structure within the shroud such that at least one inner surface of the shroud contacts at least one surface of the heat spreading structure.

25. The method of claim 24, wherein the applying of the bead line of flowable acoustic damping gel or paste comprises applying the bead line of flowable acoustic damping gel or paste in a closed loop.

26. An ultrasound device, comprising:
   an ultrasound probe housing;
   a shroud disposed at one end of the ultrasound probe housing;
   an ultrasound transducer module disposed within the shroud;
   a heat spreading structure disposed within a region defined by the shroud and the ultrasound probe housing; and
   an acoustic damping gel disposed at least partially around an inner perimeter of the shroud.

27. The ultrasound device of claim 26, wherein the acoustic damping gel is disposed as a bead line of the acoustic damping gel.

* * * * *